(12) United States Patent
Gardiner et al.

(10) Patent No.: US 7,786,073 B2
(45) Date of Patent: Aug. 31, 2010

(54) CONTAINER FOR DIETARY SUPPLEMENT HAVING IMPROVED EFFICACY AT TIME OF CONSUMPTION

(76) Inventors: Paul T. Gardiner, 5100 Spectrum Way, Mississauga, Ontario (CA) L4W 5S2; Marvin A. Heuer, 5100 Spectrum Way, Mississauga, Ontario (CA) L4W 5S2; Shan Chaudhuri, 5100 Spectrum Way, Mississauga, Ontario (CA) L4W 5S2; James D. Ramsbottom, 5100 Spectrum Way, Mississauga, Ontario (CA) L4W 5S2

( * ) Notice: Subject to any disclaimer, the term of this patent is extended or adjusted under 35 U.S.C. 154(b) by 60 days.

(21) Appl. No.: 11/443,656

(22) Filed: May 30, 2006

(65) Prior Publication Data

US 2007/0280996 A1 Dec. 6, 2007

(51) Int. Cl.
*A61K 47/00* (2006.01)
(52) U.S. Cl. .............................. 514/2; 514/19; 424/439
(58) Field of Classification Search ........................ None
See application file for complete search history.

(56) References Cited

U.S. PATENT DOCUMENTS

| 2,562,402 A | 7/1951 | Winsten |
| 2,753,990 A | 7/1956 | Chalfen et al. |
| 4,627,986 A | 12/1986 | Bardsley et al. |
| 4,760,090 A * | 7/1988 | Nissen ........................ 514/557 |
| 6,620,425 B1 * | 9/2003 | Gardiner ....................... 424/439 |
| 6,620,444 B1 | 9/2003 | Reichinger |

OTHER PUBLICATIONS

U.S. Appl. No. 11/349,960, filed Feb. 7, 2006, Gardiner et al.

* cited by examiner

*Primary Examiner*—Christopher R. Tate
*Assistant Examiner*—Roy Teller

(57) ABSTRACT

A dietary supplement that includes a container having a first compartment and a second compartment. The first compartment includes an aqueous medium. The second compartment includes an ingredient that is stable when stored within the second compartment. The container is configured such that a user may selectively cause the first and second compartments to be in communication with each other such that the ingredient of the second compartment is mixed with the aqueous medium of the first compartment. The ingredient, which may be creatine or a derivative thereof, is less stable after being mixed with the aqueous medium of the first compartment.

24 Claims, No Drawings

CONTAINER FOR DIETARY SUPPLEMENT HAVING IMPROVED EFFICACY AT TIME OF CONSUMPTION

FIELD OF THE INVENTION

The present invention relates to a dietary supplement, e.g., ready-to-drink supplements that include ingredients, e.g., creatine and derivatives thereof, which may be unstable if dissolved in an aqueous solution significantly before the dietary supplement is to be consumed. By improving the stability of such ingredients, the present invention may improve the efficacy of the ingredient at the time of consumption.

SUMMARY OF THE INVENTION

According to an embodiment of the present invention, there is provided a dietary supplement that includes a container having a first compartment and a second compartment. The first compartment includes an aqueous medium. The second compartment includes an ingredient that is stable when stored within the second compartment. The container is configured such that a user may selectively cause the first and second compartments to be in communication with each other such that the ingredient of the second compartment is mixed with the aqueous medium of the first compartment. The ingredient, which may be creatine or a derivative thereof, is less stable after being mixed with the aqueous medium of the first compartment.

According to another embodiment of the present invention, there is provided a dietary supplement that is provided in a container. A first compartment of the container includes an aqueous medium. A second compartment of the container includes at least one ingredient. The ingredient may be more stable when stored separately from the aqueous solution as compared to when dissolved in the aqueous solution. In a pre-use configuration of the container, the first and second compartments are not in communication with each other. In a use configuration of the container, e.g., immediately prior to consumption of the dietary supplement by a user, the first and second compartments are in communication with each other and the ingredient is mixed with the aqueous medium.

DETAILED DESCRIPTION OF THE INVENTION

One of the ways that an ingredient of a dietary supplement may be provided to a user is by suspending or dissolving the ingredient in an aqueous solution. While some dietary supplements may provide an ingredient pre-mixed in the aqueous solution, there are some ingredients (for example, creatine and others discussed in greater detail below) for which the suspension or dissolution of the ingredient within a solution for longer than a given period of time may undesirably alter, e.g., degrade or otherwise transform, the ingredient's molecular make-up and thus adversely effect the ingredient's function. Since the stability and/or efficacy of certain ingredients of a dietary supplement formulation can be compromised within a given amount of time after being dissolved in an aqueous solution, the present invention may improve the stability and/or efficacy of certain active ingredients by storing such ingredients in separate compartments of a single container. The separate compartments provide, prior to the consumption of the supplement, a physical barrier between the components of the dietary supplement, e.g., between the aqueous solution and the ingredient that may exhibit compromised stability and/or efficacy upon being, or within a given amount of time after being, dissolved in the aqueous solution.

To consume the supplement, a user may selectively cause the contents of the separate compartments to mix. For example, the user may deform or otherwise manipulate the two compartments such that the ingredient stored in a first compartment is mixed with the aqueous solution in the second compartment. Since the user may perform this step, e.g., mixing the ingredient stored in the first compartment with the aqueous solution in the second compartment, at the time that the dietary supplement is to be consumed, any instability and/or inefficacy which may have resulted from the ingredient being dissolved in an aqueous solution for longer than a given period of time may be avoided.

Various embodiments of the present invention may include creatine also know as (alpha-methyl) guandino-acetic acid. Creatine is one of the basic molecules involved with energy storage, particularly in fast twitch glycolytic fibres. Creatine loading is known to increase the creatine stored within muscle tissue. Moreover, creatine is able to reversibly bind phosphate. Therefore, if more creatine is present within a muscle tissue, there is more stored and donatable phosphate within the muscle tissue. When a muscle undergoes a contraction, it employs adenosine triphosphate (ATP) as an energy source. During this process a phosphate group is cleaved from ATP leaving the molecule adenosine diphosphate (ADP), which is devoid of energetic properties with respect to muscular contraction (Tortora G J, Grabowski S R. Principles of Anatomy and Physiology. $8^{th}$Ed. Addison Wesley Longman, Inc. Don Mills, ON. 1996). Creatine is able to pick-up a phosphate and reversibly bind it; forming Phospho-creatine. Phospho-creatine ultimately donates a phosphate to ADP, thus rendering ATP, which is able to be used in a subsequent muscular contraction immediately following intense muscle effort and provides enough energy for 15 seconds of maximal contraction. Therefore, creatine loading aids in the regeneration of ATP, leading to an increase in muscular output ability. (Tortora G J, Grabowski S R. Principles of Anatomy and Physiology. $8^{th}$ Ed. Addison Wesley Longman, Inc. Don Mills, ON. 1996).

Creatine converts to creatinine via an irreversible, pH-dependent, non-enzymatic reaction in aqueous medium. Aqueous and alkaline solutions contain a mixture of creatine and creatinine. In acidic solutions, 100% of creatine is converted to creatinine. While creatine plays an important role in storing high energy phosphate for muscle use, creatinine is inactive and is excreted by the kidneys (Mesa J L, Ruiz J R, Gonzalez-Gross M M, Gutierrez Sainz A, Castillo Garzon M J. Oral creatine supplementation and skeletal muscle metabolism in physical exercise. Sports Med. 2002; 32(14):903-44. Review.).

Creatine is also known as 2-(carbamimidoyl-methylamino) acetic acid, N-(aminoiminomethyl)-N-methylglycine, N-amidinosarcosine, (alpha-methylguanido) acetic acid, N-methyl-N-guanylgliycine and methylglycocyamine. Creatine as used herein may refer to creatine in any of its known forms, e.g., salts and/or esters thereof. Examples of creatine in its various forms include but are not limited to creatine monohydrate, creatine alpha ketoglutarate, creatine ethyl ester HCl, tricreatine hydroxycitrate, creatine citrate, creatine pyruvate, creatine pyroglutamate, dicreatine malate, creatine anhydrous, creatine taurinate, and creatine methyl ester.

Tricreatine hydroxycitrate is another example of a creatine derivative which may be unstable in an aqueous medium. It is formed in an anionic-cationic reaction whereby three moles of creatine are bound to one mole of hydroxycitric acid.

Applicant's co-pending U.S. patent application Ser. No. 11/349,960, for "Creatine Hydroxycitric Acid Salts and Methods for Their Production and Use in Individuals", which was filed on Feb. 7, 2006, and which is based upon U.S. Provisional Patent No. 60/651,049, filed on Feb. 7, 2005, discloses a method for producing tricreatine hydroxycitrate.

As set forth above, the present invention, in accordance with various embodiments thereof, involves a dietary supplement that is disposed in a container that has at least two compartments. In order to improve the stability and/or efficacy of an ingredient of the dietary supplement, the ingredient may be maintained in a first compartment of the container until a user selectively causes, e.g., immediately prior to consumption, the ingredient to be mixed with an aqueous solution stored in a second compartment of the container.

While the present invention envisions that any type of multi-compartmented container may be employed, some examples of two-part beverage containers are disclosed, for example, in U.S. Pat. Nos. 2,562,402, 2,753,990, 4,627,986 and 6,620,444.

U.S. Pat. No. 2,562,402, discloses a two compartment container wherein the outer container is comprised of a flexible material which upon squeezing increases the internal pressure. The inner container or capsule is pressure-sensitive and upon an increase in the internal pressure of the outer container, the inner capsule ruptures and its contents are mixed with the contents of the outer container.

U.S. Pat. No. 2,753,990, discloses a glass container having large and small-sized, separate compartments for the storage of the first and second liquids in the separate storage compartments. When the large compartment is opened, thus resulting in a drop in pressure below that of the small compartment leads to the opening of a valve in the wall separating the two compartments allowing for the mixing of the liquids in the two compartments.

U.S. Pat. No. 4,627,986, discloses a container for the storage of a pressurized fluid, having a separate compartment therein for the segregated storage of a second material. The mechanism is arranged such that it is sensitive to the rapid drop in pressure upon the opening of the container and that the contents of the segregated container are released into the fluid of the first container.

U.S. Pat. No. 6,620,444, discloses a two compartment container under pressure wherein the inner compartment opens in response to pressure change upon the opening of the outer compartment. The contents of the inner container are thus released and mixed with the contents of the outer container immediately prior to consumption.

While the preceding examples illustrate some of the types of containers that may be employed in the practice of the present invention, Examples 1 to 4 below illustrate some of the dietary supplements that may advantageously employ such containers. Generally, these dietary supplements include active ingredients that may irreversibly convert to inactive forms of the ingredient were the ingredients to be dissolved in the respective aqueous solution greater than a given period of time prior to a user consuming the dietary supplement. In this manner, the stability and/or efficacy of the ingredients may be increased by preventing the active molecules from dissolving or being suspended in the aqueous solution until a predetermined time period, e.g., immediately, prior to consumption.

Although the following examples illustrate the practice of the present invention in five of its embodiments, the examples should not be construed as limiting the scope of the invention. Other embodiments will be apparent to one skilled in the art from consideration of the specification and the following examples.

EXAMPLES

Example 1

A dietary supplement is contained within a container comprising two compartments. Within a first compartment, a solute mixture of granular anhydrous creatine (2.5000 g), calcium salt of ketoisocaproic acid (0.0500 g), and trometamol salt of alpha lipoic acid (0.1000 g) is contained. Within a second compartment, a solvent is contained. At the time of opening the two-compartment container, the contents of the first compartment are emptied, e.g., automatically, into the second compartment such that the solutes contained within the first compartment are combined with the solvent in the second compartment to form a consumable solution.

Example 2

A dietary supplement is contained within a container comprising two compartments. Within a first compartment, a solute mixture of creatine citrate (5.0170 g), trometamol salt of alpha lipoic acid (0.0510 g), creatine alpha ketoglutarate (0.0010 g), creatine ethyl ester HCl (0.0010 g), creatine methyl ester (0.0010 g), dicreatine malate (0.0010 g), granular anhydrous creatine (0.00094 g), calcium salt of ketoisocaproic acid (0.00002 g) is contained. Within a second compartment, a solvent is contained. At the time of opening the two-compartment container, the contents of the first compartment are emptied, e.g., automatically, into the second compartment such that the solutes contained within the first compartment are combined with the solvent in the second compartment to form a consumable solution.

Example 3

A dietary supplement is contained within a container comprising two compartments. Within a first compartment, a solute mixture of creatine citrate (4.9940 g), trometamol salt of alpha lipoic acid (0.0510 g), granular anhydrous creatine (0.00094 g), calcium salt of ketoisocaproic acid (0.00002 g), creatine alpha ketoglutarate (0.0010 g), creatine pyroglutamate (0.0010 g), dicreatine malate (0.0010 g), L-glutamine (0.0010 g), and taurine (0.0010 g) is contained. Within a second compartment, a solvent is contained. At the time of opening the two-compartment container, the contents of the first compartment are emptied, e.g., automatically, into the second compartment such that the solutes contained within the first compartment are combined with the solvent in the second compartment to form a consumable solution.

Example 4

A dietary supplement is contained within a container comprising two compartments. Within a first compartment, a solute mixture comprising at least tricreatine hydroxycitric acid or a derivative thereof is contained. Within a second compartment, a solvent is contained. At the time of opening the two-compartment container, the contents of the first compartment are emptied, e.g., automatically, into the second compartment such that the solutes contained within the first compartment are combined with the solvent in the second compartment to form a consumable solution.

What is claimed:

1. A dietary supplement container comprising: a first compartment and a second compartment, the first compartment including a consumable aqueous medium, the second compartment including a mixture of ingredients comprising creatine or a salt thereof, calcium salt of ketoisocaproic acid and trometamol salt of alpha lipoic acid, wherein the salt of creatine comprises at least one of creatine monohydrate, creatine alpha ketoglutarate, creatine ethyl ester HCL, tricreatine hydroxycitrate, creatine citrate, creatine pyruvate, creatine pyroglutamate, dicreatine malate, creatine anhydrous, creatine taurinate, creatine lipoate, and creatine methyl ester; whereby said mixture is stable within the second compartment, the container being configured such that a user may selectively cause the first and second compartment to be in communication with each other such that the mixture within the second compartment is combined with the consumable aqueous medium within the first compartment, the mixture being less stable after being combined with the consumable aqueous medium of the first compartment.

2. The dietary supplement container of claim 1, wherein the creatine or a salt thereof comprises at least one of creatine monohydrate, creatine alpha ketoglutarate, creatine ethyl ester HCl, tricreatine hydroxycitrate, creatine citrate, creatine pyruvate, creatine pyroglutamate, dicreatine malate, creatine anhydrous, creatine taurinate, creatine lipoate and creatine methyl ester.

3. The dietary supplement container of claim 1, wherein the second compartment comprises a mixture of granular anhydrous creatine, calcium salt of ketoisocaproic acid, and trometamol salt of alpha lipoic acid.

4. The dietary supplement container of claim 3, wherein the mixture comprises about 2.5 g of granular creatine, about 0.05 g of calcium salt of ketoisocaproic acid, and about 0.1 g of trometamol salt of alpha lipoic acid.

5. The dietary supplement container of claim 1, wherein the second compartment comprises a mixture of creatine citrate, trometamol salt of alpha lipoic acid, creatine alpha ketoglutarate, creatine ethyl ester HCl, creatine methyl ester, dicreatine malate, granular anhydrous creatine, calcium salt of ketoisocaproic acid.

6. The dietary supplement container of claim 5, wherein the mixture comprises about 5.0170 g of creatine citrate, about 0.0510 g of trometamol salt of alpha lipoic acid, about 0.0010 g of creatine alpha ketoglutarate, about 0.0010 g of creatine ethyl ester HCl, about 0.0010 g of creatine methyl ester, about 0.0010 g of dicreatine malate, about 0.00094 g of granular anhydrous creatine, about 0.00002 g of calcium salt of ketoisocaproic acid.

7. The dietary supplement container of claim 1, wherein the second compartment comprises a mixture of creatine citrate, trometamol salt of alpha lipoic acid, granular anhydrous creatine, calcium salt of ketoisocaproic acid, creatine alpha ketoglutarate, creatine pyroglutamate, dicreatine malate, L-glutamine, and taurine.

8. The dietary supplement container of claim 7, wherein the mixture comprises about 4.994 g of creatine citrate, about 0.0510 g of trometamol salt of alpha lipoic acid, about 0.00094 g of granular anhydrous creatine, about 0.0002 g of calcium salt of ketoisocaproic acid, about 0.0010 g of creatine alpha ketoglutarate, about 0.0010 g of creatine pyroglutamate, about 0.0010 g of dicreatine malate, about 0.0010 g of L-glutamine and about 0.0010 g of taurine.

9. A dietary supplement container comprising: a first compartment of the container including a consumable aqueous medium; and a second compartment of the container including a mixture of ingredients comprising creatine or a salt thereof, calcium salt of ketoisocaproic acid and trometamol salt of alpha lipoic acid, wherein the salt of creatine comprises at least one of creatine monohydrate, creatine alpha ketoglutarate, creatine ethyl ester HCL, tricreatine hydroxycitrate, creatine citrate, creatine pyruvate, creatine pyroglutamate, dicreatine malate, creatine anhydrous, creatine taurinate, creatine lipoate, and creatine methyl ester; whereby said mixture is more stable when stored separately from the consumable aqueous medium as compared to when dissolved in the consumable aqueous medium, wherein, in a pre-use configuration of the container, the first and second compartments are not in communication with each other, and wherein, in use configuration of the container, the first and second compartments are in communication with each other and the mixture is combined with the consumable aqueous medium.

10. The dietary supplement container of claim 9, wherein the creatine or a salt thereof comprises at least one of creatine monohydrate, creatine alpha ketoglutarate, creatine ethyl ester HCl, tricreatine hydroxycitrate, creatine citrate, creatine pyruvate, creatine pyroglutamate, dicreatine malate, creatine anhydrous, creatine taurinate, creatine lipoate and creatine methyl ester.

11. The dietary supplement container of claim 9, wherein the second compartment comprises a mixture of granular anhydrous creatine, calcium salt of ketoisocaproic acid, and trometamol salt of alpha lipoic acid.

12. The dietary supplement container of claim 11, wherein the mixture comprises about 2.5 g of granular anhydrous creative, about 0.05 g of calcium salt of ketoisocaproic acid, and about 0.1 g of trometamol salt of alpha lipoic acid.

13. The dietary supplement container of claim 9, wherein the second compartment comprises a mixture of creatine citrate, trometamol salt of alpha lipoic acid, creatine alpha ketoglutarate, creatine ethyl ester HCl, creatine methyl ester, dicreatine malate, granular anhydrous creatine, calcium salt of ketoisocaproic acid.

14. The dietary supplement container of claim 13, wherein the mixture comprises about 5.0170 g of creatine citrate, about 0.0510 g of trometamol salt of alpha lipoic acid, about 0.0010 g of creatine alpha ketoglutarate, about 0.0010 g of creatine ethyl ester HCl, about 0.0010 g of creatine methyl ester, about 0.0010 g of dicreatine malate, about 0.00094 g of granular anhydrous creatine, about 0.00002 g of calcium salt of ketoisocaproic acid.

15. The dietary supplement container of claim 9, wherein the second comportment comprises a mixture of creatine citrate, trometamol salt of alpha lipoic acid, granular anhydrous creatine, calcium salt of ketoisocaproic acid, creatine alpha ketoglutarate, creatine pyroglutamate, dicreatine malate, L-glutamine, and taurine.

16. The dietary supplement container of claim 15, wherein the mixture comprises about 4.994 g of creatine citrate, about 0.0510 g of trometamol salt of alpha lipoic acid, about 0.00094 g of granular anhydrous creatine, about 0.0001 g of calcium salt of ketoisocaproic acid, about 0.0010 g of creatine alpha ketoglutarate, about 0.0010 g of creatine pyroglutamate, about 0.0010 g of dicreatine malate, about 0.0010 g of L-glutamine and about 0.0010 g of taurine.

17. The dietary supplement container according to claim 1, wherein the ingredient being more stable when stored separately from the consumable aqueous medium is separated from the consumable aqueous medium having a pH less than or equal to 7.

18. A dietary supplement container according to claim 1, wherein the ingredient being more stable when stored separately from the consumable aqueous medium is separated from the consumable aqueous medium having a pH greater than or equal to 7.

19. A dietary supplement container according to claim 1, wherein the ingredient being more stable when stored separately from the consumable aqueous medium is separated from the consumable aqueous medium being more acidic than the unstable ingredient.

20. The dietary supplement container according to claim 1, wherein the unstable ingredient is separated from the consumable aqueous medium being more basic than the unstable ingredient.

21. A dietary supplement container according to claim 9, wherein the ingredient being more stable when stored separately from the consumable aqueous medium is separated from the consumable aqueous medium having a pH less than or equal to 7.

22. A dietary supplement container according to claim 9, wherein the ingredient being more stable when stored separately from the consumable aqueous medium is separated from the consumable aqueous medium having a pH greater than or equal to 7.

23. A dietary supplement container according to claim 9, wherein the ingredient being more stable when stored separately from the consumable aqueous medium is separated from the consumable aqueous medium being more acidic than the unstable ingredient.

24. A dietary supplement container according to claim 9, wherein the ingredient being more stable when stored separately from the consumable aqueous medium is separated from the consumable aqueous medium being more basic than the unstable ingredient.

* * * * *